United States Patent [19]

Boehme

[11] Patent Number: 4,922,114
[45] Date of Patent: May 1, 1990

[54] WIPER MECHANISM

[76] Inventor: Hilary Boehme, 250 N. Fehr Way, Bay Shore, N.Y. 11706

[21] Appl. No.: 360,098

[22] Filed: Jun. 1, 1989

[51] Int. Cl.$^5$ ............................................. A61L 2/10
[52] U.S. Cl. .................... 250/436; 250/435; 250/432 R; 250/428; 250/429; 250/504 R; 422/24
[58] Field of Search ............... 250/436, 435, 432 R, 250/428, 429, 504 R; 210/236, 243, 748; 313/15, 634

[56] References Cited

U.S. PATENT DOCUMENTS

| | | | |
|---|---|---|---|
| 2,667,584 | 1/1954 | Rhodes | 250/435 |
| 2,670,439 | 2/1954 | Rarney | 250/429 |
| 2,844,727 | 7/1958 | Maciszewski et al. | 250/435 |
| 3,061,721 | 10/1962 | Brenner | 250/431 |
| 3,182,191 | 5/1965 | McFarland et al. | 250/435 |
| 3,456,107 | 7/1969 | Robertson | 422/24 |
| 3,462,597 | 8/1969 | Young | 422/24 |
| 3,562,520 | 2/1971 | Hippen | 422/24 |
| 3,904,363 | 9/1975 | Free | 250/431 |
| 4,017,734 | 4/1977 | Ross | 250/435 |
| 4,151,085 | 4/1979 | Malik | 422/24 |
| 4,766,321 | 8/1988 | Lew et al. | 250/436 |
| 4,767,932 | 8/1988 | Ellner | 250/436 |

*Primary Examiner*—Janice A. Howell
*Assistant Examiner*—Kiet T. Nguyen
*Attorney, Agent, or Firm*—Leonard Belkin

[57] ABSTRACT

A liquid purification system comprising a housing with inlet and outlet for the flow of the liquid to be purified. A source of ultraviolet is mounted within the housing surrounded by a sleeve of ultraviolet-transmissive material such as quartz. A rod mounted for reciprocal movement is mounted in the housing and extends out of the housing. On the rod is mounted wiper assemblies each one of which consists of tear-shaped plate to surround the sleeve, a washer of suitable material on the plate to make contact with the sleeve for wiping the outer surface of the sleeve as the rod is reciprocated, and a securing device to hold the washer in place. Pins with press-on nuts are employed to sandwich each wiper assembly together.

8 Claims, 3 Drawing Sheets

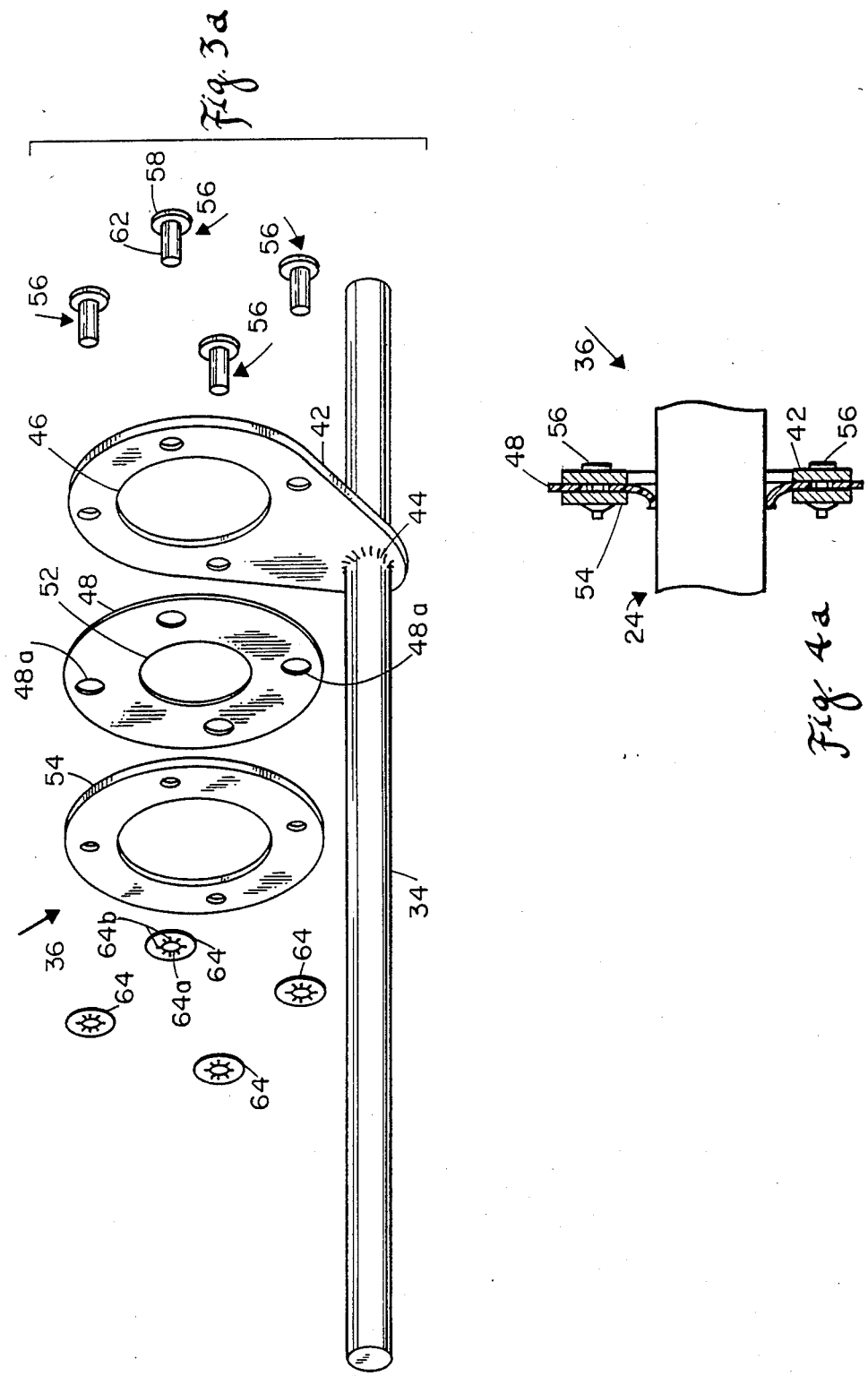

WIPER MECHANISM

BACKGROUND OF THE INVENTION

This invention relates to fluid photo reactors and more particularly to ultraviolet ray (UV) water purifiers.

In a typical irradiation type of water purifier, a quartz tube or sleeve which is circular in cross section containing the source of UV is mounted in the path of flowing water to be purified. The UV passes through the transparent wall of the sleeve and effects the elimination of bacteria, mold, virus, and algae from the water.

The use of UV for the disinfection of water has been accepted by the U.S. Public Health Service provided the equipment used meets certain listed criteria. Among the criteria listed is a specified minimum dosage of the UV and the use of equipment which includes provision to permit frequent mechanical cleaning of the water contact surface of the sleeve without disassembly of the unit. Thus, some provision must be incorporated to permit frequent cleaning of the outer surface of the quartz sleeve.

To meet the aforementioned requirement, one popular design of such a unit incorporates wiper assemblies mounted on the outside of the quartz sleeve with a rod extending outside of the unit for reciprocating the wiper assemblies periodically to clean the surface. The assemblies generally employ wiper rings which surround the quartz sleeve snugly so that movement along the length of the sleeve will result in cleaning of the surface. Some current designs for supporting the wipers are generally difficult to fabricate on an assembly line basis, and often require frequent repair and maintenance.

In addition, the quartz tubing in use is not perfectly round nor perfectly straight. For example, commercial tolerance of the outside diameter is commonly plus or minus 4% and the tube is most often out of round. Quartz tubes used in ultraviolet water purfiers now often exceed 60 inches in length and they often exhibit varying degrees of bow along the length. One consequence of the foregoing is that in typical wiper arrangements now in use there may be hit and miss contact between the wiper and the outer surface of the tube.

The following U.S. patents show present designs of irradiation devices including various ways of cleaning the surface of the transparent sleeve: U.S. Pat. Nos. 3,061,721, 3,462,597, 3,562,520, and 3,904,363. A current design is also shown in Pollution Engineering, December 1973, Ultraviolet Water Purification, by J. G. Mone, FIG. 3. None of the preceding patents or publications teaches the present invention.

SUMMARY OF THE INVENTION

In the present invention, the apparatus in an ultraviolet ray water purifier employing a transparent sleeve incorporates wiper apparatus which overcomes or minimizes many of the problems associated with previous and current designs of such wipers.

This is accomplished by stretch and fit design of flexible wiper rings of suitable material such as Teflon to compensate for out of round and dimensional variation in the quartz tube. The wiper rings are mounted in such a way as to permit the rings to move enough on their mountings to compensate for any bowing and any minor misalignment problems which may exist in the sleeve.

Other features of this invention include a design which prevents metal to glass contact between the wiper mechanism and the quartz sleeve permitting the apparatus to be shipped assembled rather than separately requiring the user to assemble the apparatus. In addition, the wiper rings are readily replaceable and ring thickness may be varied to suit varying conditions.

In accordance with a preferred embodiment of this invention there is provided a rod spaced from and extending parallel to the transparent sleeve carrying at least one but preferably more than one flat ring holder surrounding the sleeve. A wiper ring made of suitable wiper material such as Teflon is located on the flat ring holder and a securing ring is placed adjacent the wiper ring forming a sandwich construction. The holder, the wiper ring, and the securing ring are provided with holes which are aligned and through which are inserted readily releasable retaining pins. The retaining pins are locked in place by push nuts sufficiently lose to permit the wiper rings to move transversely. This construction is easy and economical to assemble or dissasemble, requires very little maintenance, and is simple to align, and stays in alignment under ordinary operating conditions.

It is therefore a principal object of this invention to provide a water irradiation assembly with improved means for wiping clean the transparent sleeve.

Other objects and advantages of this invention will hereinafter become obvious from the following description of preferred embodiments of this invention.

BRIEF DESCRIPTION OF THE DRAWINGS

FIG. 3a is an exploded view of the holder.

FIG. 4a is a view similar to FIG. 4 showing the holder in place.

DETAILED DESCRIPTION OF THE PREFERRED EMBODIMENTS

Figure 1:
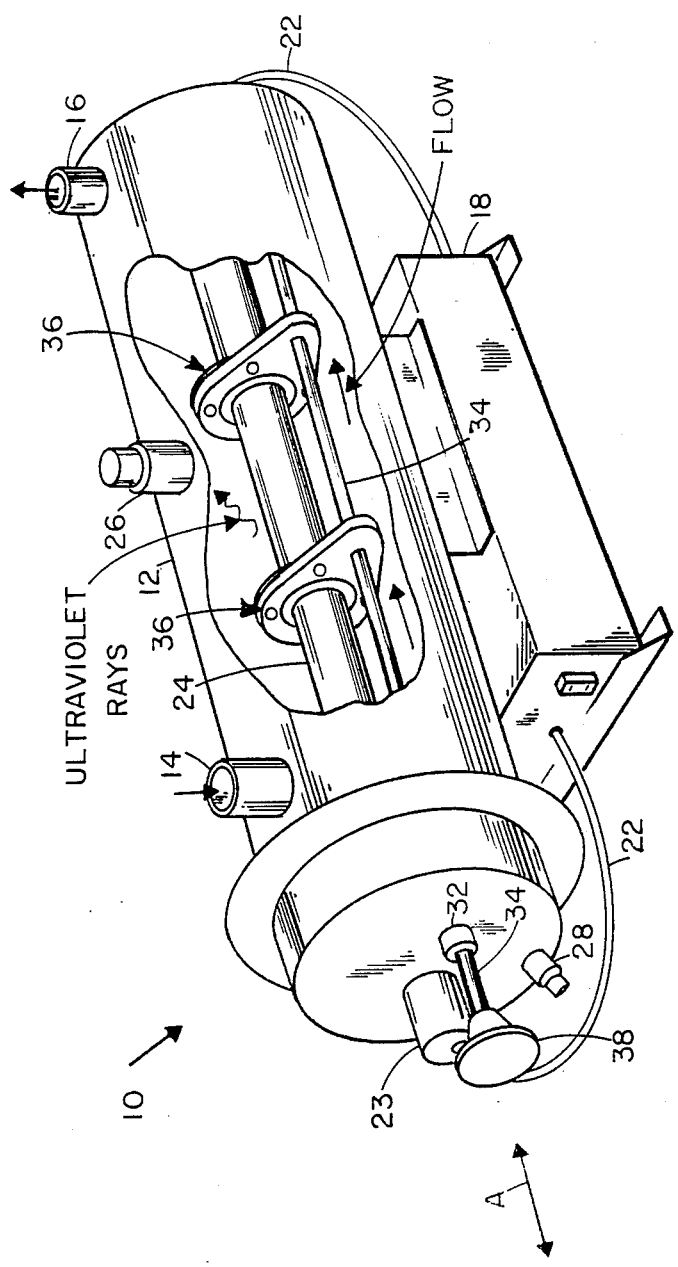
FIG. 1 is an isometric view partially cut away of water purification apparatus incorporating the principles of this invention.

Referring to FIG. 1, water purifier 10 consists of a cylindrical housing 12 with inlet 14 for water to be purified and an outlet 16 for the water. Housing 12 is mounted on a transformer housing and junction box 18, supplying electrical power through electrical leads 22 to the germacidal lamp 23 extending into transparent sleeve or tube 24. Lamp 23 provides the source of UV for the purification of the water. As is understood in the art sleeve or tube 24 would be made of suitable ultraviolet-transmissive material and, typically, this would be quartz having the proper qualities.

Housing 12 would also be provided with a sight port 26 to view the condition of lamp 23 and sleeve 24, a drain 28, and an opening 32 for wiper rod 34 passing into housing 12.

For cleaning the outer surface of transparent sleeve 24, attached to rod 34 are a number of wiper assemblies 36. The end of rod 34 extending out of housing 12 terminates in a wiper knob 38 which is used to reciprocate rod 34 and wiper assemblies 36 as indicated by double headed arrow A to wipe periodically the outer surface of sleeve 24.

Figure 4:
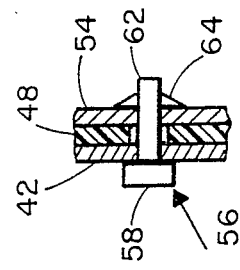
FIG. 4 is a section view along 4—4 of FIG. 3
Figure 2:
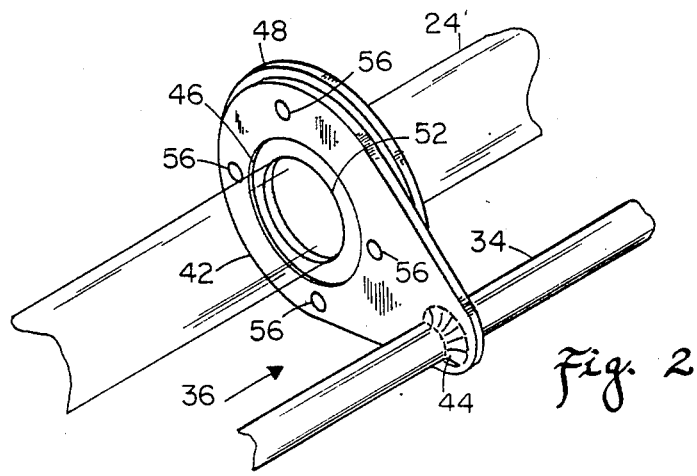
FIG. 2 is an isometric view of a single wiper and holder employed in the preferred embodiment of this invention.
Figure 3:
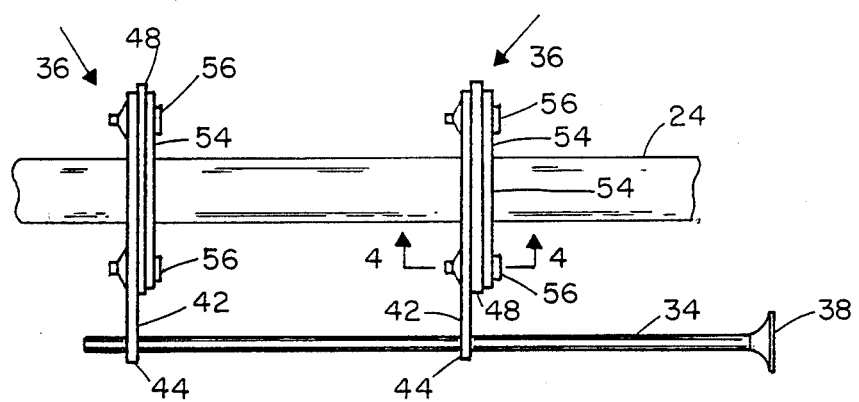
FIG. 3 is a side elevation view of the holder shown in FIG. 2.

For details of wiper assemblies 36 constructed in accordance with this invention, reference is made to FIGS. 2, 3, 3a 4 and 4a. Each assembly 36 consists of a flat wiper support 42 of tear drop configuration with its narrowest portion provided with an opening for rod 34 and welded at 44 to rod 34. Holder 42 is provided with a circular opening 46 through which transparent sleeve 24 passes. On one side or face of support 42 is the wiper ring 48 whose opening 52 is circular and whose diameter is such as to have ring 48 make contact with the outer surface of sleeve 24 in the manner described as stretch to fit shown in FIG. 4a. By stretch to fit herein is meant that opening 52 in wiper ring 48 is slightly less than the outside diameter of quartz sleeve 24 and that the material from which wiper ring 48 is sufficiently flexible that upon mounting of assembly 36, wiper ring 48 will curl up against sleeve 24 as shown in FIG. 4a. This curling has the added advantage of providing greater surface contact for a given wiper ring which enhances the cleaning effect as assembly 36 is moved along the length of sleeve 24 by push rod 34, and also aids in compensating for out of round and dimensional variation in the quartz tube.

Placed on ring 48 is a back up ring 54. Wiper support 42, wiper ring 48, and back up ring 54 are provided with a plurality of aligned openings to accomodate pins 56. Openings 48a in wiper ring 48 are slightly oversized as seen in FIG. 4 for a reason to be described below. Each pin 56 consists of a head 58 with a barrel 62 extending through support 42, ring 48, and ring 54. A readily releasable push nut 64 is employed to hold the assembly together. Each nut 64 has an opening 64a and radially extending slits 64b. It is seen that with the construction just described it is simple to take apart assembly 36 to replace wiper ring 48 when required; also, with the holes for pins 56 properly aligned initially, ring 48 is automatically aligned upon being mounted and stays that way during ordinary operation of the apparatus.

It was pointed out that openings 48a in wiper ring 48 are oversized. The purpose of this construction is to permit wiper ring 48 some movement at right angles to the length of sleeve 24 to compensate for any bowing in the latter and minor alignment problems. To facilitate this movement, during installation of pins 56, push nuts 64 are not made snug against heads 58 of pins 56. That is, pins 56 are loosely mounted by which is meant herein that pins 56 are sufficiently loosely mounted to permit transverse movement of wiper rings 48 between back up ring 54 and wiper support 42 as wiper assemblies 36 are moved down the length of sleeve 24 by push rod 34. Hence, the spacing between wiper support 42 and back up ring 54 can be adjusted to apply an optimum combination of support and freedom of movement for each wiper 48.

When the wiper ring is reinforced by being supported in the sandwiched assembly as herein described, greater tension of the wiper ring against the quartz sleeve results, producing enhanced wiping action and improved removal of deposits from the quartz sleeve.

Figure 5:
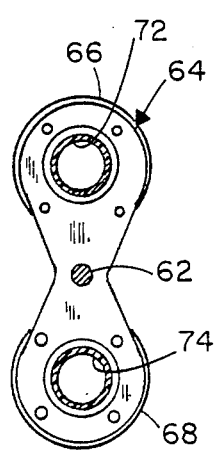
FIG. 5 is a frontal view of a wiper assembly which is an alternative embodiment of this invention.
Figure 6:
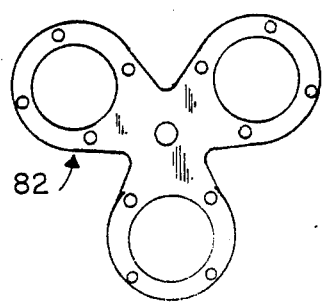
FIGS. 6 & 7 a view similar to that of FIG. 5 showing two other alternative embodiments.
Figure 7:
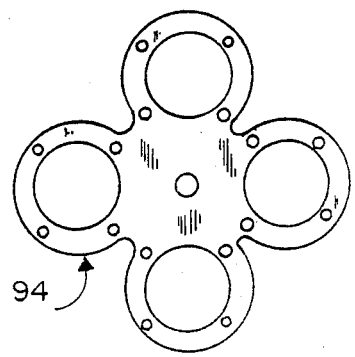

One of the advantages of this invention is that it is possible to employ a single rod and wiper assembly to wipe more than one transparent sleeve. For example, referring to FIG. 5 there is shown mounted on rod 62 a double-lobed ring holder 64 to support a pair of wiper rings 66 and 68 to simultaniously wipe a pair of transparent sleeves 72 and 74 mounted within a single purifier (not shown). In a similar fashion, FIG. 6 illustrates a triple-lobed ring holder 82 for three transparent sleeves and FIG. 7 illustrates a quadruple-lobed ring holder 94 for cleaning four sleeves at a time.

It is thus seen that there has been provided a unique cleaning assembly for use in water purifiers. While only certain preferred embodiments of this invention have been described it is understood that many variations are possible without departing from the principles of this invention as defined in the claims which follow.

What is claimed is:

1. In liquid purification apparatus comprising housing means having inlet and outlet means for the liquid to be purified to enter and leave said housing means, source means mounted within said housing to produce ultraviolet radiation, extended sleeve means of ultraviolet-transmissive material surrounding said source means to permit the transmission of ultraviolet radiation into said liquid flowing around said sleeve means, rod means extending along the length of and spaced from said sleeve means, said rod means extending out of said housing means and mounted for movement along its length, the improvement comprising assembly means mounted on said rod means within said housing means for cleaning the outer surface of said sleeve means as said rod means is reciprocated, said assembly means comprising:
  a. wiper support means attached adjacent one end to said rod means and having an opening through which said sleeve means passes, said opening being sufficiently large so as to be spaced from said sleeve means around the outer surface of the latter;
  b. wiper means mounted on one side of said wiper support means surrounding said sleeve means and making stretch to fit contact with the outer surface of said sleeve means;
  c. back up ring means mounted on said wiper means so that said back up ring means and said wiper support means sandwich said wiper means; and
  d. a plurality of readily releasable means mounted through a plurality of holes arranged around said sleeve means aligned through said wiper support means, wiper means, and back up ring means to secure said wiper means in continuous contact with said sleeve means during reciprocal movement of said rod means to effect the cleaning of the surface of said sleeve means.

2. The apparatus of claim 1 wherein said wiper means includes first means to permit transverse movement of said wiper means with respect to said back up ring means and said wiper support means when said rod means if reciprocated to compensate for any bowing along the length of said sleeve means.

3. The apparatus of claim 2 wherein said first means comprises said openings in said wiper means through which said readily releasable means pass being over sized to permit said transverse movement, said wiper means being sufficiently loosely mounted to permit said transverse movement during normal operation.

4. The apparatus of claim 1 wherein said support means is pear-shaped and attached through an opening at its narrowest point to said rod means passing through the latter said opening.

5. The apparatus of claim 1 wherein multiple wiper assemblies are mounted on said rod means.

6. The apparatus of claim 1 wherein said readily releasable means comprises an unthreaded pin with a head at one end, and a push nut on the other end.

7. The apparatus of claim 1 wherein said support means includes multiple openings to accomodate more than one sleeve means within said housing, said support means being provided with wiper means and back up ring means for each of said openings.

8. The apparatus of claim 1 wherein said releasable means can be adjusted to apply an optimum combination of support and freedom to said wiper ring.

* * * * *